United States Patent
Shelley et al.

(10) Patent No.: US 7,800,069 B2
(45) Date of Patent: Sep. 21, 2010

(54) METHOD FOR PERFORMING IR SPECTROSCOPY MEASUREMENTS TO DETERMINE COATING WEIGHT/AMOUNT FOR METAL CONVERSION COATINGS

(75) Inventors: Paul H. Shelley, Lakewood, WA (US); Gregory J. Werner, Puyallup, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 12/189,113

(22) Filed: Aug. 8, 2008

(65) Prior Publication Data

US 2010/0032573 A1 Feb. 11, 2010

(51) Int. Cl.
*G01J 5/02* (2006.01)
(52) U.S. Cl. .................................. 250/341.8
(58) Field of Classification Search ............... 250/341.8, 250/339.01, 339.09, 339.11, 370.07, 341.1
See application file for complete search history.

(56) References Cited

U.S. PATENT DOCUMENTS

| | | | |
|---|---|---|---|
| 5,091,647 A * | 2/1992 | Carduner et al. ....... | 250/339.09 |
| 5,795,394 A * | 8/1998 | Belotserkovsky et al. ... | 118/665 |
| 6,784,431 B2 | 8/2004 | Shelley et al. | |
| 6,794,651 B2 | 9/2004 | Shelley et al. | |
| 6,984,825 B2 * | 1/2006 | Shelley et al. .......... | 250/339.11 |
| 7,115,869 B2 | 10/2006 | Shelley et al. | |
| 7,119,336 B2 * | 10/2006 | Allen et al. ............ | 250/339.11 |
| 7,223,977 B2 | 5/2007 | Shelley et al. | |
| 2003/0230720 A1 * | 12/2003 | Shelley et al. ............ | 250/341.8 |
| 2003/0232448 A1 * | 12/2003 | Shelley et al. ............... | 436/164 |
| 2004/0099807 A1 * | 5/2004 | Shelley et al. .......... | 250/339.01 |
| 2009/0321647 A1 * | 12/2009 | Shelley et al. .......... | 250/339.07 |

* cited by examiner

*Primary Examiner*—David P Porta
*Assistant Examiner*—Faye Boosalis
(74) *Attorney, Agent, or Firm*—Tung & Associates (57) ABSTRACT

A method of determining a coating weight and/or amount of a conversion coating on a metallic substrate including making near-IR spectra of a series of coating weight standards on an appropriate substrate material to match sample material in question, pre-processing the data to prepare it for multivariate calibration methods, performing the multivariate calibration, saving the calibration model in the hand-held near-IR device in an appropriate format, and using the calibration model to predict sample material in question from their near IR spectra.

23 Claims, 4 Drawing Sheets

METHOD FOR PERFORMING IR SPECTROSCOPY MEASUREMENTS TO DETERMINE COATING WEIGHT/AMOUNT FOR METAL CONVERSION COATINGS

FIELD OF THE INVENTION

This invention generally relates to Infrared (IR) measurement methods and apparatus, and more particularly provides a method for performing non-destructive IR spectroscopy measurements of surface characteristics of materials including determining a coating weight and/or amount of a metal surface treatment film (metal conversion coating), such as anodize and/or Alodine coating weight and/or amounts on an aluminum substrate.

BACKGROUND OF THE INVENTION

IR spectroscopy measurements may be useful for a variety of purposes including aerospace, automotive and industrial applications, as well as biological and bio-medical applications. For example, infrared (IR) radiation is readily absorbed by materials in association with relative motions (vibrations) of atoms such as carbon, hydrogen, oxygen and nitrogen. As such, IR spectroscopy measurements may indicate a condition of a wide variety of organic as well as inorganic materials.

For example, frequently it is necessary to determine the coating weight of a coating material on a substrate, to verify that the film coating weight is sufficient, including but not limited to, anodized coatings on metallic substrates. For example, aluminum aircraft parts often receive an anodized coating or a surface treatment including second metals for corrosion resistance and for enhanced paint adhesion, referred to herein respectively as an anodize coating and an Alodine coating. Generally, a uniform coating amount within an acceptable range is desired.

Prior art methods for measuring metal surface treatment film amounts (e.g., anodize and/or Alodine coating) include time consuming and destructive testing approaches that include coating the aluminum substrate, then weighing the substrate and coating, then stripping the coating from the substrate, and then weighing the substrate again. Because the test method is destructive, it cannot be used on the manufactured product. In addition, the currently known testing process only generates a spatially averaged coating amount for the sample. As such, the currently known testing process does not determine coating amount variations over an area.

Another approach includes the use of a portable IR device that includes an IR filtering device to filter IR signals from the substrate to monitor a narrow portion of the IR spectrum around 10.98 microns to determine a weight of the coating, as outlined in co-owned U.S. Pat. Nos. 6,784,431 and 6,984,825) which are hereby incorporated by reference. In this method, an infrared beam is reflected off the metallic substrate to form a reflected beam and the reflected beam is filtered to a predetermined wavelength band and then detected. The infrared energy of the reflected beam is compared with a predetermined value of infrared energy reflected off the metallic substrate without the anodize coating to determine an absorbance value for the anodize coating. The absorbance value for the anodize coating at a target wavelength of 10.89 microns is then correlated to an amount of the anodize coating.

Drawbacks in the above approach include the expense of the IR filtering device and relatively limited diagnostic information included in the IR spectrum employed including the narrow filtered portion of the spectrum detected and monitored at a target wavelength of 10.89 microns representing an Aluminum-Oxygen-Aluminum vibrational stretch. Differences in surface reflectivity between calibration standards and samples in question can lead to measurement errors when using filter IR methods.

Other infrared (IR) non-destructive methods in the prior art used to measure the properties of thin films include using IR absorbance to determine the amount of a chromated conversion coating on a metallic substrate (U.S. Pat. No. 6,794,631), determining an amount of chemical cure and amount of surface contamination (U.S. Pat. No. 6,906,327), determining the amount/thickness of an opaque coating on a substrate (U.S. Pat. No. 6,903,339) and (U.S. Pat. No. 7,223,977), and determining an amount of heat damage to a resin-fiber composite substrate (U.S. Pat. No. 7,115,869), all of which are fully incorporated herein by reference.

None of the above methods and associated devices, however, disclose a method or device that is suitable for performing IR spectroscopy including determining a coating weight and/or amount of a converted metal coating (conversion coating) such as an anodize and/or Alodine film coating on a metal substrate using robust multivariate calibration methods, particularly where a portable, real-time capability is desirable, such as in aircraft manufacturing, assembly, maintenance, and repair of aircraft.

Thus, there is a continuing need for improved IR non-destructive testing methods including a method or device that is suitable for performing IR spectroscopy including determining a coating weight and/or amount of a conversion coating such as an anodize and/or Alodine film coating on a metal substrate using multivariate calibration methods, particularly where a portable, real-time capability is desirable, such as in aircraft manufacturing, assembly, maintenance, and repair of aircraft.

Therefore it is an object of the invention to provide a method or device that is suitable for performing IR spectroscopy including determining a coating weight and/or amount of a conversion coating such as an anodize and/or Alodine film coating on a metal substrate using multivariate calibration methods, particularly where a portable, real-time capability is desirable, such as in aircraft manufacturing, assembly, maintenance, and repair of aircraft.

SUMMARY OF THE INVENTION

A method of determining a coating weight and/or amount (e.g., in terms of coating weight in $mg/ft^2$) of a conversion coating on a metallic substrate is provided, the method includes obtaining the IR spectra of a series of film coating weight standards and building a multivariate calibration model with the spectra of those standards. An infrared spectrum obtained from the coating film which is in question can then be predicted by the multivariate model to determine the coating weight of the film.

These and other objects, aspects and features of the invention will be better understood from a detailed description of the preferred embodiments of the invention which are further described below in conjunction with the accompanying Figures.

DETAILED DESCRIPTION OF THE PREFERRED EMBODIMENT

The present invention achieves the foregoing objects, aspects and features by providing a method of non-destructively determining the coating weight of a film coating on a substrate where the method may be accomplished by making an infrared (IR) spectroscopy measurement with an IR spectrometer over a spectrum of wavelengths in the near-IR or mid-IR, preferably with a portable IR spectrometer, and performing a multivariate calibration on a series of collected IR spectra (reflected spectra) from as series of calibration standards and then using the multivariate calibration model to predict the film coating weight of samples in question, including as part of an manufacturing, assembly, maintenance, or repair process of an aircraft.

It will be appreciated that although the invention is particularly explained with reference to using IR spectroscopy to determine a coating weight and/or amount of an inorganic film on a substrate such as an anodize aluminum coating on aluminum surfaces used in portions of aircraft, that the invention may additionally be advantageously used to quantify a coating weight and/or amount of an inorganic film coating on a substrate in general, particularly metallic substrates.

While either a portable or non-portable IR spectrometer may be used to carry out the IR spectroscopy measurements according to the present invention, in a preferred embodiment a near-IR spectrum of wavelengths, e.g., including the range of about 900 to 1700 nanometers and/or about 1600 to about 2400 nanometers, is used to make the IR spectroscopy measurement according to the present invention. It will be appreciated that a mid-IR spectrum of wavelengths may be additionally or alternatively used having a range from about 2.5 to about 15.4 microns. Further, in a preferred embodiment, a hand-held portable spectrometer capable of performing near-IR spectroscopy measurements is used to perform the IR spectroscopy measurements according to the present invention. The term near-IR refers to a spectrum of wavelengths from about 900 to about 2400 nanometers.

The hand-held portable IR spectrometer may have the capability to supply source IR energy to a sample at a predetermined incident angle between about 30 to about 60 degrees, and collect reflected light from the sample through a broad range of angles which may exclude the incident angle. The hand-held portable IR device preferably has the ability to make diffuse reflectance IR spectroscopic measurements (also referred to as an external reflectance IR spectroscopic measurement).

Figure 1:
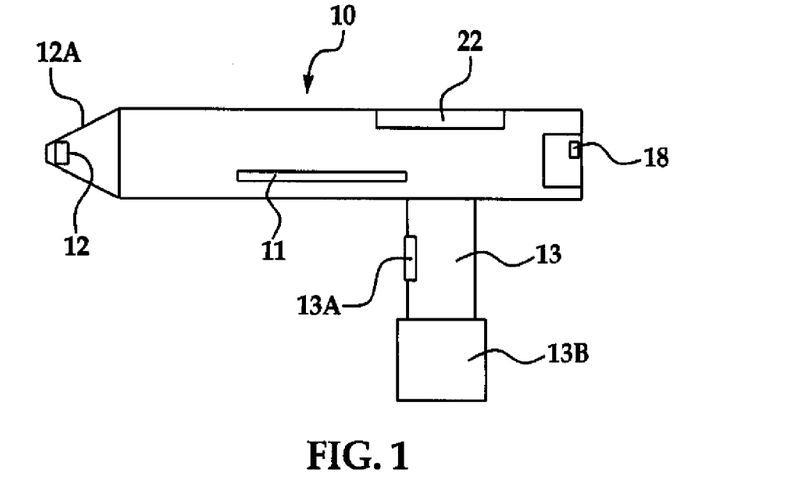
FIG. 1 is a schematic diagram of an exemplary hand-held portable IR spectrometer suitably used to make IR spectroscopy measurements according to an embodiment of the invention.

Referring to FIG. 1 is shown a side view of a portable (handheld) IR spectrometer 10 according to an embodiment of the invention. The portable IR spectrometer 10 preferably has the capability of performing near-IR spectroscopy measurements. By the term portable (handheld), is meant an instrument that may be easily carried and picked up and moved about to make IR spectroscopy measurements by an average person, e.g., has a weight of less than about 8 pounds and may be hand-held and aimed (or held against) a location on the measurement surface to make a spot-size measurement.

The portable IR spectrometer 10 also preferably includes a microprocessor and memory (e.g. micro-processor board 11) and may be interfaced (placed in communicated with) with other computing devices (e.g., USB port 18). The portable IR spectrometer 10 may be supplied power by one or more batteries (e.g., 13B in handle portion 13). The portable IR spectrometer 10 is preferably programmable and/or capable of accepting, storing, and executing preprogrammed instructions for carrying out IR spectroscopy measurements. The portable IR spectrometer 10 preferably has the capability to provide incident IR light (energy) and collect reflected IR spectra over an operating wavelength range (e.g., about 900 nanometers to about 2400 nanometers and/or 2.5 to 15.4 microns) and to store the spectra and perform mathematical manipulation of the data comprising the spectra including performing multivariate analysis of the spectra. It will be appreciated that an external computer or controller may also be used with the IR spectra loaded to the computer/controller from the spectrometer that will be used in the calibration. Following multivariate calibration of the spectra, the Regression Coefficients are downloaded to the spectrometer to make predictions with respect to coatings of interest. Preferably, the spectrometer is capable of doing spectra data pre-processing as is needed for the predictions.

In one embodiment, the portable IR spectrometer 10 may have an elongated front portion 12A which includes one or more IR transparent energy windows e.g., 12, for example the IR transparent energy window may have an alterable and/or predefined size spectrometer 10 with respect to a measurement surface to make a spot size IR spectroscopy measurement of a pre-defined size. For example, an IR-transparent window 12, may be set back from the surface of the nose portion 12A, which may be placed on or close to the surface of the sample to be measured to produce a known spot-size measurement area, e.g., which may be any size but preferably ranges from an area of about 1 $mm^2$ to about 1 $cm^2$ or alternatively having a spot diameter for a round spot of about 1 to 5 mm. In some embodiments, the nose portion 12A may be an interchangeable IR probe, including different IR spectrum ranges and/or measurement spot sizes, and may include IR transparent fiber optics.

In addition, the portable IR spectrometer 10 may include additional sample measurement interfaces as are known in the art for fitting over the more IR transparent energy windows e.g., 12, for providing incident IR energy to a sample over a range of pre-defined defined angles and/or a predetermined spot size and for collecting reflected IR energy from the sample over a range of pre-defined angles, preferably to make a diffuse reflectance measurement (e.g., where an incident IR energy angle equal to a reflected IR energy angle is excluded from collection).

The portable IR spectrometer 10 may include a triggering device e.g. 13A on handle portion 13 for triggering an IR spectroscopy measurement or the IR spectroscopy measurement may be alternately triggered e.g., by softkeys on an interactive LCD touchscreen 22. It will be appreciated that the portable IR spectrometer 10 may be of any suitable ergonomic shape to enhance the portability and ease of holding and manipulating the spectrometer to carryout hand-held IR spectroscopy measurements.

The portable IR spectrometer 10 preferably has the ability to store collected IR spectra and perform mathematical manipulation of the data comprising the spectra including multivariate data pre-processing of the spectra. The portable IR spectrometer 10 may include interactive buttons and/or softkeys e.g., on an interactive LCD or LED touchscreen 22, or elsewhere, and may include a textual display to guide the operator through an IR spectroscopy measurement process.

In addition, suitable calibration background reference standard materials and wavelength reference standard materials may be provided for calibrating the IR spectrometer prior to performing IR spectroscopy measurements according to embodiments of the invention.

In one embodiment, an IR spectrometer used to carry out an IR spectroscopy measurement according to the present invention, such as the portable IR spectrometer 10, may be provided and have stored in memory one or more calibration models for use in a subsequent IR spectroscopy measurement and multivariate prediction processes where the calibration model is with respect to material in a similar condition to an area of the sample with a known level (e.g. baseline including the absence of), the property to be measured, such as a known coating weight and/or amount, but at least preferably a known coating weight of, a metal surface treatment film, such as an anodize film coating on a metallic substrate or a metal surface corrosion resistant treatment agent. For example, it has been found that wavelengths in the near-IR range, e.g., a spectrum of wavelengths from about 900-2400 nanometers, and 2.5 to 15.4 microns are particularly useful for determining the coating weight of an inorganic film coating such as a converted metal surface coating (conversion coating), which may include a roughened interface with the metal substrate. It has been found that the near-IR spectrum is essentially blind to the conversion coating interface roughness when the proper data pre-processing is used.

It will be appreciated that the use of the term metal surface treatment film or converted metal film (conversion film) includes oxidized metal surfaces such as anodized metal surfaces having a thin (e.g., 0.1 to 3 microns) anodize film coating which may be formed by conventional electro-chemical anodization processes and/or surface applied chemicals (e.g., including treatment with acids) which may chemically cause oxidation of the metal surface to form a thin anodize film. For example, the metals surface treatment film or conversion film may additionally or alternatively include metal surface treatments, such as treatment of the metal substrate surface with commercially available adhesion promoting (to promote adhesion of overlying layers such as paint) and/or corrosion resistance treatments which may include one or more second metals such as one or more of Cr, Mn, Mo, Si, Ti, and Zr which may form a film coating on the metal surface, such as e.g., commercially available Alodine™ type treatments for treating aluminum surfaces (referred to herein as an Alodine film coating).

It will be appreciated that the metal surface treatment film, such as Alodine, may include second metals as well as a polymer material. For example, the metal surface treatment film, also referred to herein as a conversion film, may include a portion of the surface of the metal substrate converted into a second material, such as an oxidized metal substrate and/or a surface treatment film including second metals, such as chrome compounds as generally found in Alodine.

For example, anodization processes for forming anodize films (anodized metal surfaces) preferably includes a boric sulfuric acid anodization process (BSAA), but may include other anodization processes which form thin glassy films on a metal substrate surface such as Sulfuric Acid Anodize (SAA), Phosphoric Acid Anodize (PAA) and Chromic Acid Anodize (CAA).

In an important aspect of the invention, a previously determined multivariate calibration model of IR spectra versus coating weight and/or amount, preferably correlated with a coating weight, of a metal surface treatment film may be stored in memory within the IR spectrometer. For example, the predetermined calibration model may be determined by calibrating a plurality of model IR spectra (absorbance and/or reflectance at one or more wavelengths in the near-IR wavelength spectrum) with a known coating weight and/or amount of a metal surface treatment film (conversion film) from a respective plurality of model standards where the known coating weight and/or amount of the metal surface treatment film for each of the model samples is determined by separate and independent measurements, e.g., one or more of optical microscopy, electron microscopy, weigh—strip—weigh, and X-ray analysis. It will be appreciated that Alodine and anodize coating weights are generally determined in $mg/ft^2$ by using 3 inch square test coupons that are coated and weighed and the coating is then striped off with concentrated acid and the coupons are weighed again to determine the weight of the coating. Calculations may then be done to find milligrams per square foot ($mg/ft^2$) for the coating.

As such, an IR spectrometer, such as portable IR spectrometer 10, may be calibrated such that an in-situ (real-time) analysis of collected IR spectra taken from an actual manufactured sample may be performed to determine a coating weight and/or amount of the metal surface treatment film in a non-destructive manner. Preferably, a quantified (numerical) level of the metal surface treatment film coating weight and/or amount may be determined in real-time by a portable IR spectrometer, such as the IR spectrometer 10, and stored and/or output. Additionally or alternatively, a pass/fail type determination (metal surface treatment film weight and/or amount above or below a threshold numerical value) and a resulting indication thereof may stored and/or output.

The portable IR spectrometer 10, or another IR spectrometer used to carry out IR spectroscopy measurements according to embodiments of the invention, preferably includes a computer processor (or an associated controller) capable of multivariate calibration of the IR spectra. For example, the IR spectrometer (or an associated controller) preferably has the ability to mathematically and statistically correlate and determine changes in a plurality of variables (e.g., IR spectra including reflectance at a plurality of wavelengths) with respect to one or more reference IR spectra. For example, the calibration may be accomplished by transferring calibration spectra from the spectrometer to a separate associated computer where the multivariate calibration is done. The regression coefficients are then transferred back into the spectrometer to perform a multivariate prediction step on new spectra from samples in question. The spectrometer is preferably capable of performing pre-processing of new spectra (derivatives, smoothing, etc.) prior to performing a dot product of the regression coefficients with the properly processed spectra. In addition, multivariate statistical approaches may be used to correlate the statistically determined changes in the plurality of variables (e.g., absorbance and/or reflectance at one or more wavelengths) with one or more independently determined second variables (e.g. a change in coating weight and/or amount of an inorganic material containing coating such as a metal surface treatment film including an aluminum anodize film coating and/or Alodine film coating).

There are many suitable multivariate techniques that may be used to make an IR spectroscopy measurement according to the present invention including, but not limited to, quantification methodologies, such as, partial least squares, principal component regression ("PCR"), linear regression, multiple linear regression, stepwise linear regression, ridge regression, radial basis functions, and the like.

In addition, suitable multivariate statistical approaches include classification methodologies, such as, linear discriminant analysis ("LDA"), cluster analysis (e.g., k-means, C-means, etc., both fuzzy and hard), and neural network ("NN") analysis.

Further, it will be appreciated that there are several data processing methods that may be suitably used to in connection with suitable multivariate statistical approaches including smoothing, taking first and second derivatives of the IR spectra, and peak enhancement methods.

In addition, multivariate calibration of collected IR spectra may include the selection and clustering together of groups of wavelengths on which to perform a regression analysis to determine a corresponding change in the IR spectra (spectrum) (e.g., reflectance) with respect to reference spectra (spectrum). It will be appreciated that an individual IR spectrum may be formed from several IR spectra (e.g., by averaging techniques known in the art). In addition, the raw IR spectra may transformed into second IR spectra by taking first and/or second derivatives and performing smoothing and/or peak enhancement as well as carrying out regression analysis. For example, manipulation the raw IR spectra by smoothing algorithms prior to or following taking a first derivative and then quantifying a degree of change of the IR spectra from a reference spectrum (similarly processed) according to a regression or partial least squares analysis may be performed.

In addition, the IR spectroscopy measurement process may include collecting reference IR spectra (including calculated absorbance and/or reflectance) which may serve as a standard from which to determine relative changes in sample IR spectra by multivariate calibration. In addition, various processing methods as are known in the art may be used to form a single IR spectrum from a collection of a plurality of collected IR spectra, including various averaging techniques, for example to improve a signal to noise ratio, prior to carrying out multivariate calibration to determine a change from a reference spectrum. It will be appreciated that the change from the reference spectrum may include a change at one or more wavelengths including clusters of wavelengths.

Figure 2A:
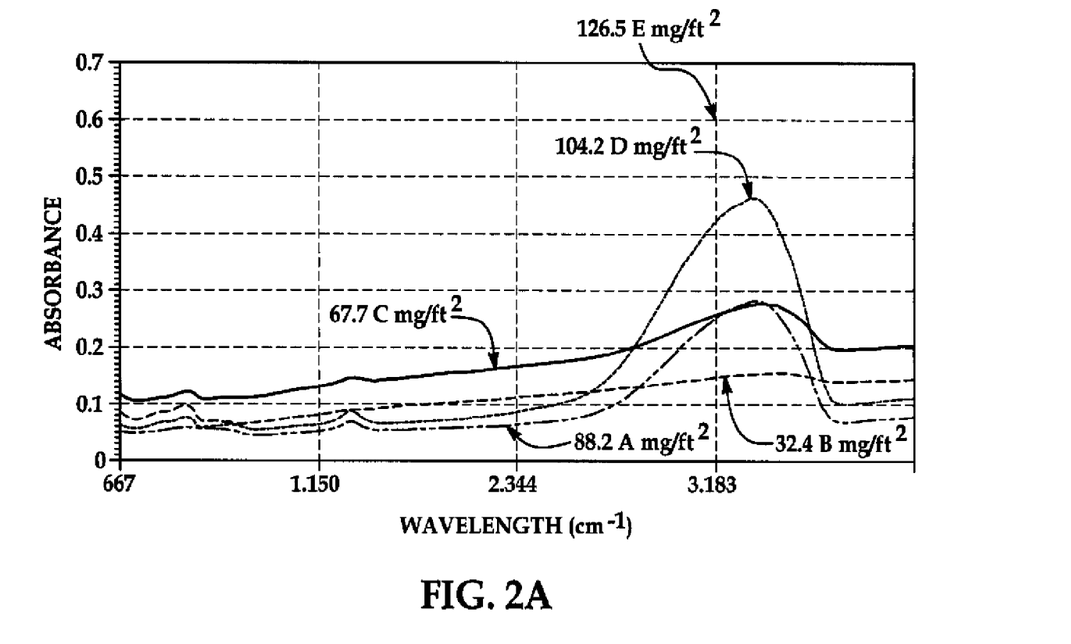
FIG. 2A is an exemplary series of IR spectra subjected to multivariate calibration with respect to a reference spectrum according to an embodiment of the invention.

Referring to FIG. 2A is shown a series of exemplary IR spectra following transformation of the raw sample IR spectra with a baseline correction. Shown are exemplary spectra A, B, C, D, and E with an associated coating amount (weight/area) of Alodine on a metal substrate.

Figure 2B:
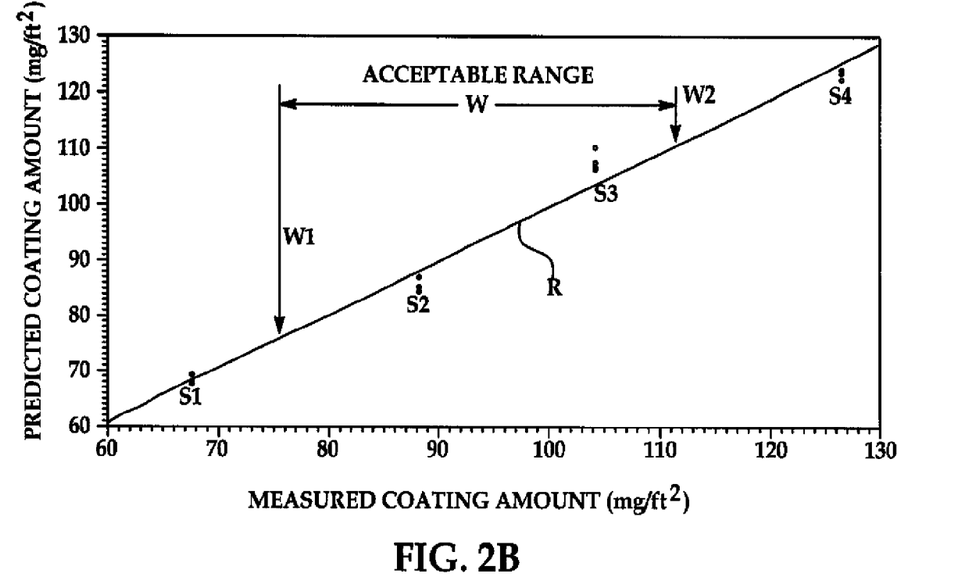
FIG. 2B shows data points of an exemplary conceptual predetermined multivariate calibration of several model IR spectroscopy measurements performed on coating weight standard samples and correlated to a coating weight and/or amount of a composition ingredient of a film coating according to an embodiment of the invention. This plot is the predicted coating weight versus the measured coating weight for multiple IR readings on each coating weight standard.
Figure 2C:
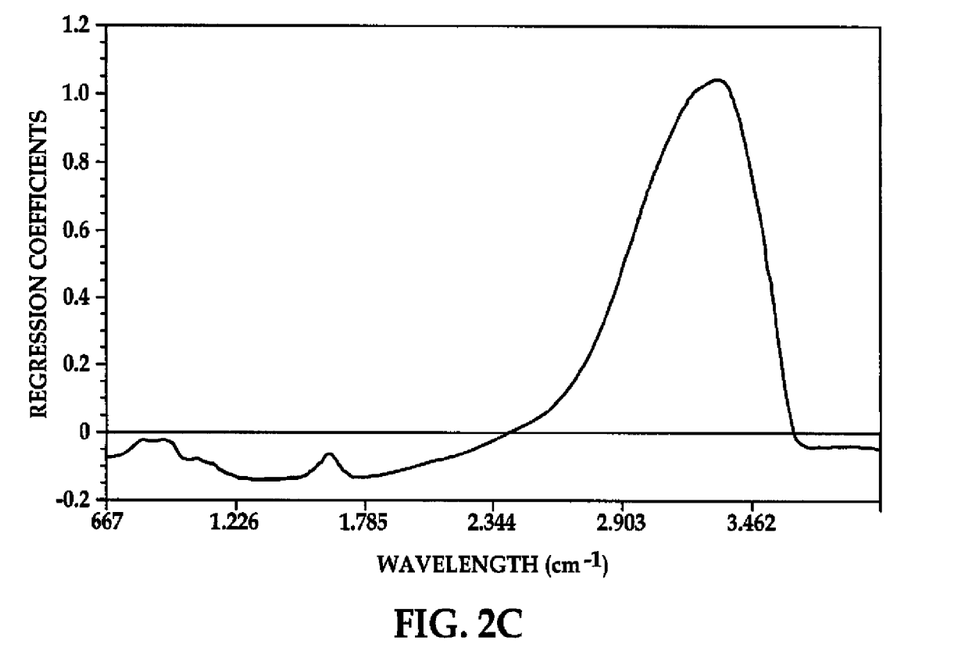
FIG. 2C shows exemplary conceptual vector of regression coefficients for the multivariate calibration model that are used to predict the coating weight and/or amount of samples in question by making the dot product of the new spectra with the regression coefficients vector.

Referring to FIG. 2B is shown a conceptual exemplary calibration plot of a plurality of model mid-IR spectroscopy measurements e.g., S1, S2, S3, and S4 taken from model samples with a known metal surface treatment film coating amount (weight/area). The plot represents a calibration line R which represents a predicted coating amount (weight/area) (Y-axis) (predicted by using regression coefficients vector shown in FIG. 3C as explained below) versus measured coating amount (x-axis) using a standard leave-one-out cross validation method.

In one embodiment, the film coating may be a metal surface treatment film (inorganic containing material) that is formed contiguous with a metallic surface (substrate). For example, the metallic surface may include an aluminum surface with an anodize film and/or an Alodine film, such as a surface treated aluminum portion of an aircraft. In addition, the metal surface treatment film (e.g., anodize film) may form a roughened interface with the metal substrate, e.g., including locally penetrating portions of the anodized surface treatment film. It has been found that the near-IR spectrum used according to embodiments of the invention is effectively blind to the micro-roughness of the film interface following appropriate data pre-processing methods such as derivatives and smoothing techniques that take out the baseline slope.

For example, by analyzing the data according to multivariate calibration for IR spectra from sample standards with a known coating weight (e.g., per unit area) and doing the multivariate regression of IR spectra versus coating weight to generate a multivariate calibration model for the spectra and coating weight data, and then using the regression coefficients from that model to perform a dot product with new spectra from samples in question, a quantifiable coating weight and/or amount of the metal surface treatment film may be determined. Thus, the quality or acceptability of the metal surface treatment film may be advantageously determined in real-time and in-situ (e.g., in a maintenance or manufacture environment) with a hand-held portable IR spectrometer in a manufacturing or maintenance process.

For example, referring to FIG. 2C, is shown an exemplary vector 205 of regression coefficients as a function of wavelength representing a multivariate calibration model for the coating weight standards used in the model with respect to FIG. 2B. For example the vector represents a partial least squares (PLS) calibration. The predetermined regression coefficients are used as a dot product with the sample IR spectroscopy measurements for samples in question to determine (predict) a specific coating weight and/or amount as shown in FIG. 2B.

In one embodiment, a specified range of coating weight and/or amount value W may be imposed on the predicted coating weight results, so that the IR spectroscopy measurements can then be determined (estimated) to have a coating weight and/or amount within an acceptable range. For example referring to FIG. 2B, in the exemplary sample IR spectroscopy measurement, S2 and S3 show a coating weight and/or amount between range values W1 and W2, and the coating weight and/or amount of the metal surface treatment film may be determined to be acceptable and the operator of the IR spectrometer notified by an audible and/or visual indication. Thus, the measurements S2 and S3 are determined in-situ and in real-time to represent an acceptable film coating weight and/or amount following IR spectroscopic collection, multivariate prediction, and comparison to a predetermined correlation including the superimposed coating weight range. On the other hand, measurements S1 and S4, falling outside acceptable range values W1 and W2, may be similarly determined to have an unacceptable metal surface treatment film weight and/or amount and the operator similarly notified.

It will be appreciated that an IR spectrometer used to make the measurement, such as hand-held portable IR spectrometer 10, may be programmed to keep track of a running average of an estimated film coating weight and/or amount according to several individual IR spectroscopic measurements made over a defined measurement area to determine whether an averaged determined coating weight and/or amount of the film coating over the measurement area falls within an acceptable or unacceptable range.

Figure 3:
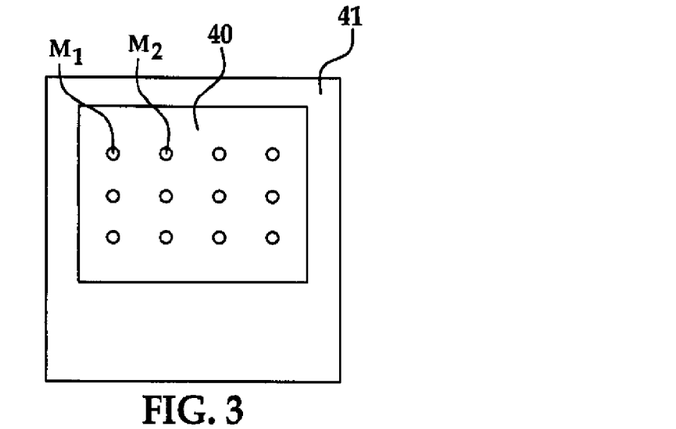
FIG. 3 shows an exemplary IR spectroscopy spot measurement process to map a film coating surface according to an embodiment of the invention.

Referring to FIG. 3, an exemplary IR spectroscopy measurement process is shown including an exemplary mapping of an exemplary metal surface treatment film e.g., anodize and/or Alodine film coating 40 on an aluminum surface 41 (underneath film coating 40). For example, following calibrating the IR spectrometer 10, a plurality of IR spectroscopy spot measurements e.g., M1, M2 (e.g., defined spot size of from 1 $mm^2$-10 $mm^2$ or a defined spot diameter from about 1 mm to about 5 mm) may be made sequentially or randomly over a predetermined area of the film coating surface. A coating weight and/or amount of the sample measurement area may be generated by mapping a determined coating weight and/or amount with respect to each spot IR spectroscopy measurement and/or a running average coating weight and/or amount may be sequentially determined for several IR spectroscopy measurements. It will be appreciated that the IR spectroscopy measurement spots e.g., M1, M2, may be any shape and where the noted spot sizes approximate a defined IR spectroscopic measurement area for an individual IR spectroscopy measurement.

Figure 4:
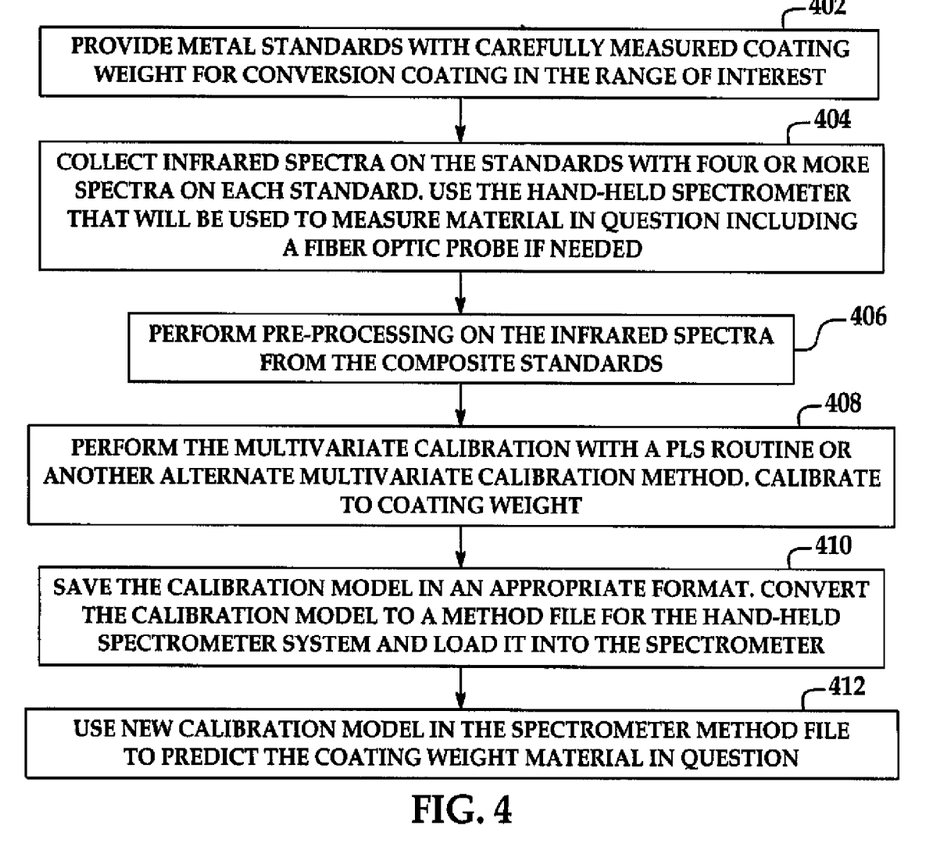
FIG. 4 is an exemplary process flow diagram including embodiments of the invention.

In an exemplary IR spectroscopy measurement process, referring to FIG. 4, in step 402 a series of coating weight/amount standards (e.g., weight per unit area) are obtained for use in the calibration. In step 404 multiple IR spectra are collected on each standard (e.g., over near-IR wavelength range 1600-2400 nm) e.g., using a reference sample with a bare substrate (e.g., metal) similar in surface topology (roughness) to the measurement samples to make an appropriate reference for the measurements. The standards must have a known coating weight and/or amount of the film coating on the substrate).

In step 406, the data pre-processing is performed on the spectra of the calibration standards in order to prepare the spectra for a good calibration model.

In step 408, a multivariate calibration model is made with the sample spectra and the known film coating weight and/or amount determined by an independent measurement.

In steps 410 and 412, the calibration model is saved in a format that is useful for the hand-held spectrometer and it is down-loaded into the spectrometer system for use in prediction coating weight and/or amount for samples in question.

Figure 5:
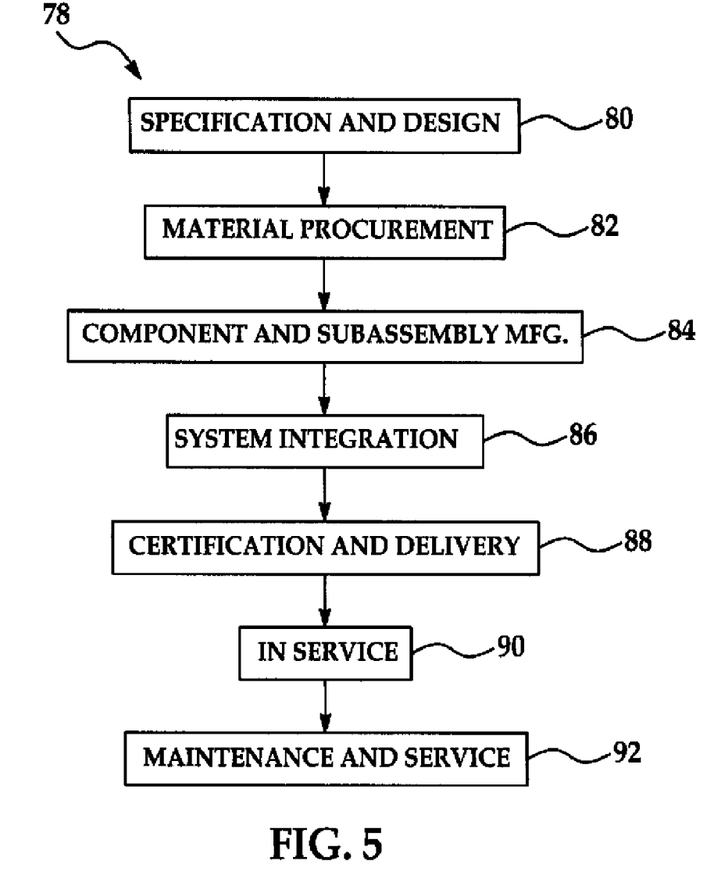
FIG. 5 is a flow diagram of an aircraft and service methodology according to an embodiment of the invention.
Figure 6:
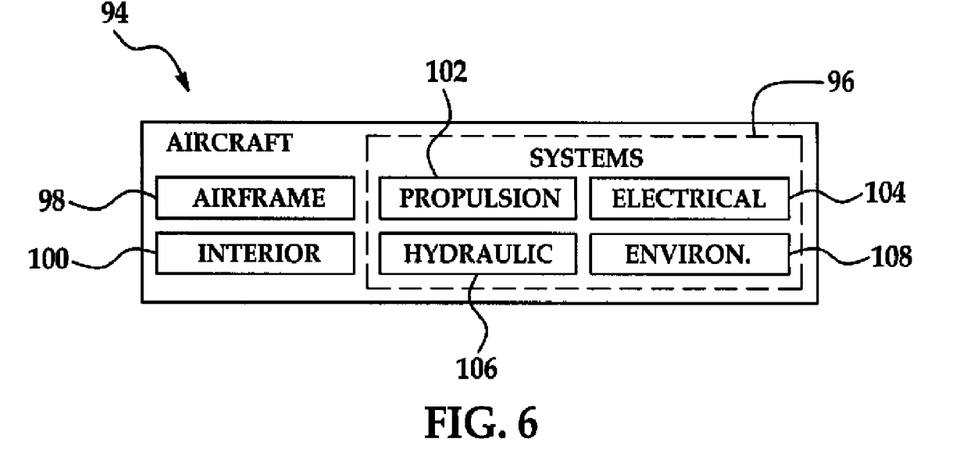
FIG. 6 is a block diagram of an aircraft according to an embodiment of the invention.

Referring next to FIGS. 5 and 6, embodiments of the disclosure may be used in the context of an aircraft manufacturing and service method 78 as shown in FIG. 5 and an aircraft 94 as shown in FIG. 6. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 6, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method of determining a weight and/or amount of a conversion coating on a metallic substrate comprising:
    irradiating said conversion coating with infrared energy over a single broadband spectrum of wavelengths;
    collecting and detecting sample infrared energy spectra reflected from said conversion coating on said substrate over each wavelength of said spectrum of wavelengths;
    providing a predetermined calibration model comprising a calibration with respect to model infrared energy spectra comprising said spectrum of wavelengths collected from a plurality of metallic substrate standards and a respective known conversion coating weight and/or amount for each metallic substrate standard, said predetermined calibration model comprising a regression coefficient at each wavelength of said model spectrum numerically processed with each corresponding respective sample spectrum wavelength to create a numerical product at each wavelength of said spectrum; and,
    determining said conversion coating weight and/or amount based on said predetermined calibration model and said sample infrared energy spectra.

2. The method of claim 1, wherein providing said predetermined calibration model comprises using multivariate statistical approaches to determine changes in absorbance and/or reflectance values at selected groups of wavelengths comprising said spectrum of wavelengths, said changes with respect to a reference spectrum.

3. The method of claim 1, wherein said conversion coating comprises oxidized surface of said metallic substrate.

4. The method of claim 1, wherein said conversion coating comprises a second metal different from said metallic substrate.

5. The method of claims 1, wherein said conversion coating is selected from the group consisting of an anodize coating and an Alodine coating.

6. The method of claims 1, wherein said metallic substrate comprises aluminum.

7. The method of claim 1, wherein said step of irradiating said conversion coating is preceded by providing a reference spectrum over said spectrum of wavelengths from a reference sample wherein said conversion coating is absent or present at a known weight and/or amount.

8. The method of claim 1, wherein said steps of providing and determining comprise:
providing a plurality of said metallic substrate standards each having said known conversion coating weight and/or amount within a pre-determined range;
collecting and detecting said infrared spectra on each of the metallic substrate standards at each wavelength of said spectrum; and
performing multivariate calibration on said infrared spectra to create said predetermined calibration model comprising a vector of said regression coefficients, said predetermined calibration model able to predict a weight and/or amount of said conversion coating of a sample metallic substrate with an unknown weight or amount of said conversion coating, said calibration model comprising said numerical product, said numerical product comprising a dot product of IR spectra collected from said metallic substrate standards with said vector of regression coefficients, said dot product created at each wavelength of said spectrum.

9. The method of claim 1, wherein said spectrum of wavelengths is from about 1600 to about 2400 nanometers.

10. The method of claim 1, wherein said steps are performed by a hand-held portable IR spectrometer.

11. The method of claim 1, wherein said steps of irradiating and detecting are performed over a pre-determined area on said conversion coating.

12. The method of claim 1, wherein said steps comprise a process selected from the group consisting of aircraft manufacturing, aircraft assembly, aircraft maintenance, and aircraft repair.

13. A method of determining a weight and/or amount of a conversion coating on a metallic substrate comprising:
providing a reference spectrum over a single broadband spectrum of wavelengths from a reference sample wherein said conversion coating is absent or present at a known weight and/or amount;
irradiating said conversion coating with infrared energy over said spectrum of wavelengths;
collecting and detecting sample infrared energy spectra reflected from said conversion coating on said substrate over each wavelength of said spectrum of wavelengths;
providing a predetermined calibration model comprising a calibration with respect to model infrared energy spectra comprising said spectrum of wavelengths collected from a plurality of metallic substrate standards and a respective known conversion coating weight and/or amount for each metallic substrate standard, said predetermined calibration model comprising a regression coefficient at each wavelength of said model spectrum numerically processed with each corresponding respective sample spectrum wavelength to create a dot product at each wavelength of said spectrum; and,
determining said conversion coating weight and/or amount based on said predetermined calibration model and said sample infrared energy spectra.

14. The method of claim 13, wherein providing said predetermined calibration model comprises using multivariate statistical approaches to determine changes in absorbance and/or reflectance values at selected groups of wavelengths comprising said spectrum of wavelengths, said changes with respect to said reference spectrum.

15. The method of claim 13, wherein said conversion coating comprises an oxidized surface of said metallic substrate.

16. The method of claim 13, wherein said conversion coating comprises a second metal different from said metallic substrate.

17. The method of claims 13, wherein said conversion coating is selected from the group consisting of an anodize coating and an Alodine coating.

18. The method of claims 13, wherein said metallic substrate comprises aluminum.

19. The method of claim 13, wherein said spectrum of wavelengths is from about 1600 to about 2400 nanometers.

20. The method of claim 13, wherein said steps are performed by a hand-held portable IR spectrometer.

21. The method of claim 13, wherein said steps of irradiating and detecting are performed over a pre-determined area on said conversion coating.

22. The method of claim 13, wherein said steps comprise a process selected from the group consisting of aircraft manufacturing, aircraft assembly, aircraft maintenance, and aircraft repair.

23. A method of determining a weight and/or amount of a conversion coating on a metallic substrate with a hand-held portable IR spectrometer comprising:
providing a plurality of said metallic substrate standards each having said known conversion coating weight and/or amount within a pre-determined range;
collecting and detecting infrared spectra comprising a single broadband spectrum of wavelengths on each of the metallic substrate standards with said hand-held portable IR spectrometer;
performing multivariate calibration on said infrared spectra at each wavelength of said spectrum to create a predetermined calibration model comprising a vector of regression coefficients, said vector of regression coefficients comprising a regression coefficient at each wavelength of said spectrum;
providing a sample metallic substrate comprising an unknown weight or amount of said conversion coating;
irradiating said conversion coating with infrared energy over said spectrum of wavelengths with said hand-held portable IR spectrometer;
collecting and detecting sample infrared energy spectra reflected from said conversion coating on said substrate over each wavelength of said spectrum of wavelengths;
providing said predetermined calibration model and creating a dot product of said vector of regression coefficients with said sample spectra, said dot product created at each wavelength of said spectrum; and,
determining said conversion coating weight and/or amount based on said dot product.

\* \* \* \* \*